(12) United States Patent
Enyong et al.

(10) Patent No.: US 11,566,010 B2
(45) Date of Patent: Jan. 31, 2023

(54) SINGLE STEP PROCESS FOR PRODUCTION OF 2-METHYLTETRAHYDROFURAN FROM FURFURYL ALCOHOL

(71) Applicant: PENN A KEM, LLC, Memphis, TN (US)

(72) Inventors: Arrey B. Enyong, Lakeland, TN (US); Shridhar G. Hegde, Germantown, TN (US)

(73) Assignee: Penn A. Kem, LLC, Memphis, TN (US)

( * ) Notice: Subject to any disclaimer, the term of this patent is extended or adjusted under 35 U.S.C. 154(b) by 23 days.

(21) Appl. No.: 17/237,132

(22) Filed: Apr. 22, 2021

(65) Prior Publication Data

US 2022/0340536 A1    Oct. 27, 2022

(51) Int. Cl.
*C07D 307/08*    (2006.01)
*C07C 29/17*     (2006.01)
*B01J 23/44*     (2006.01)
*B01D 39/20*     (2006.01)
*B01J 21/18*     (2006.01)
*B01J 38/00*     (2006.01)
*B01J 21/04*     (2006.01)

(52) U.S. Cl.
CPC ....... *C07D 307/08* (2013.01); *B01D 39/2003* (2013.01); *B01J 21/04* (2013.01); *B01J 21/18* (2013.01); *B01J 23/44* (2013.01); *B01J 38/00* (2013.01); *C07C 29/17* (2013.01)

(58) Field of Classification Search
None
See application file for complete search history.

(56) References Cited

U.S. PATENT DOCUMENTS

2011/0263880 A1* 10/2011 Rauchfuss ........... C07D 307/36
549/506
2014/0243562 A1  8/2014 Omeis et al.

OTHER PUBLICATIONS

King et al., "An Investigation of the Effect of the Addition of Tin to 5%Pd/TiO2 for the Hydrogenation of Furfuryl Alcohol," Chem Cat Chem, vol. 7, Issue14, pp. 122-2129, Jul. 13, 2015.
The International Search Report and Written Opinion, dated Jun. 24, 2022, in the related PCT Appl. No. PCT/US22/25457.
Peng et al., "Catalytic upgrading of renewable furfuryl alcohol to alkyl levulinates using AlC13 as a facile, efficient, and reusable catalyst," Fuel, vol. 160, Jul. 31, 2015, pp. 123-131.

* cited by examiner

*Primary Examiner* — Medhanit W Bahta

(57) ABSTRACT

Provided is a single step process for producing 2-methyl-tetrahydrofuran from furfuryl alcohol with high conversion rate and high selectivity towards 2-methyltetrahydrofuran.

14 Claims, No Drawings

SINGLE STEP PROCESS FOR PRODUCTION OF 2-METHYLTETRAHYDROFURAN FROM FURFURYL ALCOHOL

FIELD OF THE INVENTION

This disclosure pertains to the field of the production of 2-methyltetrahydrofuran from furfuryl alcohol by a single step process. All documents cited or referred to below are expressly incorporated herein by reference.

BACKGROUND 2-methyltetrahydrofuran (CAS No. 96-47-9, also referred as MeTHF in this disclosure) is currently used as solvent in organic chemistry.

Recent studies show that MeTHF can be a good alternative to hexane for the extraction of oil, in particular food oil. Indeed, MeTHF has the advantages to be biodegradable, to have a promising environmental footprint, to be easy to recycle, to not be classified as toxic for the environment.

In addition, unlike hexane, MeTHF is not toxic in ingestion for the amounts envisaged in food oil. In fact, a published test of 3 months of ingestion in rats showed a dose with Non Observed Adverse Effect Limit (NOAEL) of 250 mg/kg body weight/day against 23 mg/kg body weight/day for hexane (Parris et al. Regulatory Toxicology and Pharmacology 87 (2017) 54-63 and Notice of the European Scientific Committee for Food published on 17 Jun. 1994).

MeTHF has also the advantages to be produced from renewable raw materials since furfuryl alcohol, its main reactant, can be obtained from biomass. More specifically MeTHF results from the following two successive catalytic hydrogenations:

1) catalytic hydrogenation of furfuryl alcohol into 2-methylfuran in vapor phase, and
2) catalytic hydrogenation of 2-methylfuran into MeTHF in liquid phase.

The second catalytic hydrogenation is costly since it requires to first isolate 2-methylfuran from the products of the first catalytic hydrogenation. Therefore, the production cost of MeTHF from furfuryl alcohol is very high and said cost has to be reduced so that MeTHF can be considered as an economically viable alternative to hexane.

One idea to reduce the production cost of MeTHF is to avoid the second catalytic hydrogenation and to produce MeTHF directly from furfuryl alcohol.

King, et al. Chem Cat Chem 2015, 7, 2122-2129 discloses that furfuryl alcohol can be converted into MeTHF by catalytic hydrogenation in liquid phase using tin-palladium catalysts. However, the MeTHF production yield is below 25%, i.e. is very low.

US 2014/0243562 discloses the conversion of furfuryl alcohol into MeTHF by catalytic hydrogenation in liquid phase at 25° C. and 2 bar. The catalyst is a platinum oxide based catalyst. The selectivity towards MeTHF is very low since it is 6% and 12%.

Therefore, there is a need for a process which produces MeTHF from furfuryl alcohol with a high selectivity toward MeTHF and high yield thereby decreasing the production cost of MeTHF.

Surprisingly, the Applicant has developed a process that meets this need.

SUMMARY OF THE INVENTION

It is thus proposed a process for producing 2-methyltetrahydrofuran from furfuryl alcohol, comprising the following step:

a) contacting furfuryl alcohol with hydrogen in presence of a catalytic system in a liquid solvent to obtain a reaction mixture comprising 2-methyltetrahydrofuran and the catalytic system, characterized in that the catalytic system comprises a supported metal catalyst and a Lewis acid.

Advantageously, the catalytic system of the proposed process enables to produce directly 2-methyltetrahydrofuran (also referred as MeTHF) from furfuryl alcohol in a liquid phase and in a single step.

In addition, the yield and the selectivity of the conversion toward MeTHF of furfuryl alcohol by the proposed process are advantageously high while the reaction conditions are mild. Indeed, after 3 hours, a conversion of furfuryl alcohol above 99% and a selectivity toward MeTHF above 80% can be reached at a pressure of 3.5 bar and a temperature of 60° C. Therefore, the proposed process is industrially viable and decreases the production cost of MeTHF.

DETAILED DESCRIPTION

According to one aspect, it is proposed a process for producing 2-methyltetrahydrofuran from furfuryl alcohol, comprising the following step:

a) contacting furfuryl alcohol with hydrogen in presence of a catalytic system in a liquid solvent to obtain a reaction mixture comprising 2-methyltetrahydrofuran and the catalytic system, characterized in that the catalytic system comprises a supported metal catalyst and a Lewis acid.

As used herein, the term "Lewis acid" refers to a compound that accepts an electron pair.

As used herein, the term "supported metal catalyst" refers to a catalyst comprising a metal having hydrogenation catalytic activity and a support, said metal being dispersed upon said support.

It is known that contacting, in liquid phase, furfuryl alcohol with hydrogen in the presence of a hydrogenation catalyst may convert furfuryl alcohol into several compounds such as 2-methyltetrahydrofuran (also referred as MeTHF), 2-methylfuran (MeF), tetrahydrofurfuryl alcohol (THFA) and tetrahydrofuran (THF). Without being bound by any theory, the inventors are of the opinion that the catalytic system, in particular the Lewis acid, of the proposed process shifts the selectivity of the conversion of furfuryl alcohol toward MeTHF.

The Lewis acid used in the proposed process may be chosen from aluminium triflate, boron trifluoride, bis(oxalato)boric acid, cyanuric chloride, iron trichloride, iron trichloride hexahydrate, iron(II) dodecyl sulfate, iron(III) dodecyl sulfate, lithium tetrafluoroborate, magnesium bromide, magnesium triflate, scandium triflate, silver triflate, tin tetrachloride, tin tetrachloride pentahydrate, zinc tetrafluoroborate, zinc triflate and mixtures thereof, in particular from aluminium triflate, boron trifluoride, bis(oxalato)boric acid, cyanuric chloride, iron trichloride, iron trichloride hexahydrate, iron(II) dodecyl sulfate, iron(III) dodecyl sulfate, lithium tetrafluoroborate, scandium triflate, silver triflate and mixtures thereof, more particularly the Lewis acid may be chosen from boron trifluoride, bis(oxalato)boric acid, cyanuric chloride, iron(II) dodecyl sulfate, iron(III) dodecyl sulfate, lithium tetrafluoroborate and mixtures thereof, even more particularly the Lewis acid may be chosen from iron(II) dodecyl sulfate, iron(III) dodecyl sulfate, lithium tetrafluoroborate and mixtures thereof.

During step a), the Lewis acid acts as a catalyst of the hydrogenation reaction of furfuryl alcohol and do not react with furfuryl alcohol. During step a), the amount of Lewis acid is thus advantageously low.

For example, the amount of Lewis acid may be 0.001 mole to 0.20 mole equivalents with respect to furfuryl alcohol, in particular 0.01 mole to 0.08 mole equivalents with respect to furfuryl alcohol, more particularly 0.025 mole to 0.065 mole equivalents with respect to furfuryl alcohol.

The amount of Lewis acid may be adapted to the Lewis acid used in the proposed process.

For example, the amount of Lewis acid may be 0.001 mole to 0.20 mole equivalents with respect to furfuryl alcohol, in particular 0.03 mole to 0.08 mole equivalents with respect to furfuryl alcohol, more particularly 0.05 mole to 0.065 mole equivalents with respect to furfuryl alcohol. This amount is adapted to boron trifluoride, bis(oxalato) boric acid, iron(II) dodecyl sulfate, iron(III) dodecyl sulfate, lithium tetrafluoroborate and mixtures thereof.

The amount may also be 0.001 mole to 0.10 mole equivalents with respect to furfuryl alcohol, in particular 0.02 mole to 0.05 mole equivalents with respect to furfuryl alcohol, more particularly 0.025 mole to 0.035 mole equivalents with respect to furfuryl alcohol. This amount is adapted to cyanuric chloride.

Advantageously, an amount of Lewis acid in these low ranges is sufficient to convert furfuryl alcohol at high conversion rate and with high selectivity toward MeTHF. Moreover, if the amount of Lewis acid is above these ranges, then the cost of the proposed process increases thereby increasing the production cost of MeTHF.

The metal of the supported metal catalyst may be chosen from chromium, manganese, iron, cobalt, nickel, copper, zinc, molybdenum, ruthenium, rhodium, palladium, tin, platinum and mixtures thereof, in particular iron, cobalt, nickel, copper, ruthenium, rhodium, palladium, tin, platinum and mixtures thereof, more particularly the metal is palladium, cobalt, tin and mixtures thereof, even more particularly the metal may be palladium.

Palladium is particularly suited as metal of the supported metal catalyst since it gives high conversion rate and high MeTHF selectivity under mild conditions of hydrogenation.

Typically, the support of the supported metal catalyst may be chosen from, alumina ($Al_2O_3$), aluminoborate ($AlBO_3$), aluminosilicate ($Al_2SiO_5$), amberlyst, boric acid ($H_3BO_3$), carbon, sulfonated carbon ($C-SO_3H$), carbon nitride ($C_3N_4$), ceria ($CeO_2$), hydrotalcite, silica ($SiO_2$), titania ($TiO_2$), zeolite, zirconia ($ZrO_2$) and mixtures thereof, in particular alumina ($Al_2O_3$), carbon, hydrotalcite, silica ($SiO_2$), titania ($TiO_2$) and mixtures thereof, more particularly alumina, carbon, silica and mixtures thereof, even more particularly the support may be alumina, carbon or mixture thereof.

Alumina and carbon are preferred since the conversion rate and selectivity toward MeTHF of the supported metal catalyst comprising them are good, they are easy availability on commercial scale and they are cheap.

For example, the content of metal in the supported metal catalyst relative to the support may be 0.1 wt % to 10 wt %, in particular 1 wt % to 7 wt %, more particularly 4.8 wt % to 5.2 wt %.

These ranges of metal content appear to be the best balance between the activity of the catalyst and its cost. Indeed, if the content of metal in the catalyst is above these ranges then the slight increase of the reaction rate is not sufficient to compensate the significant increase of the price of the catalyst thereby decreasing its industrial interest. On the contrary, if the content of metal in the catalyst is lower, the metal coating on the support might not be fully achieved, thereby decreasing its activity and its industrial interest.

The supported metal catalyst may be synthesized by any synthesis techniques known by the skilled person. Such techniques are, for example, co-precipitation, co-gelation, ion exchange, impregnation, deposition from a vapor phase or deposition from an atomic source.

The preferred method is the impregnation of the support with a solution or suspension of the transition metal. According to this preferred method, an inorganic salt of the metal such as, for example, acetate, carbonate, chloride, nitrate or sulfate, is dissolved in water to obtain a salted solution. The salted solution has a metal amount corresponding to the desired final weight percentage of metal on the support. The solution is dropped onto the support, then recovered to be dried, and finally calcinated at high temperature so as to obtain the transition metal catalyst.

According to one embodiment, the amount of supported metal catalyst may be 1 wt % to 25 wt % with respect to furfuryl alcohol, in particular is 2 wt % to 8 wt % with respect to furfuryl alcohol, more particularly 4.5 wt % to 5.5 wt % with respect to furfuryl alcohol.

An amount of supported metal catalyst in these ranges is sufficient to advantageously convert furfuryl alcohol at high conversion rate and with high selectivity toward MeTHF. Moreover, if the amount of supported metal catalyst is above these ranges, then the cost of the proposed process increases thereby decreasing its industrial interest.

The liquid solvent that may be used during step a) of the proposed process may be any liquid solvent that is chemically compatible with the Lewis acid.

As used herein, the term "chemically compatible" means that the liquid solvent does not react with the Lewis acid. The skilled person knows if a liquid solvent is chemically compatible with the Lewis acid.

For example, the liquid solvent may be chosen from acetonitrile, dichloroethane, dimethylformamide (DMF), ethanol, ethyl acetate, isopropanol, methanol, methyl tert-butyl ether (MTBE), MeTHF, tetrahydrofuran (THF) and mixtures thereof, in particular ethyl acetate, isopropanol, methanol, MeTHF and mixtures thereof, more particularly may be MeTHF.

MeTHF may be the liquid solvent and the product of step a). Therefore, the amount of MeTHF involved during step a) is higher than when MeTHF is not the liquid solvent.

The weight ratio liquid solvent:furfuryl alcohol may be 1:0.01 to 1:10, in particular 1:0.15 to 1:5, more particularly 1:0.3 to 1:2.5, even more particularly 1:0.5 to 1:1.5.

Step a) of the proposed process is advantageously carried out under mild reaction conditions.

For example, during step a), the pressure may be 0.5 bar to 10 bar, in particular 2 bar to 5 bar, more particularly 3 bar to 4 bar.

For example, during step a), the temperature may be 0° C. to 100° C., in particular 25° C. to 70° C., more particularly 55° C. to 65° C.

Advantageously, these mild reaction conditions are sufficient to convert furfuryl alcohol at high conversion rate and with high selectivity toward MeTHF.

Step a) may typically be carried out in batch mode or continuously, in particular continuously.

An autoclave is a suitable catalytic reactor to carry out step a) in batch mode.

Fixed-bed reactor, reverse flow tubular reactors or fluidized bed reactors are suitable catalytic reactors to carry out step a) continuously. A fixed-bed reactor is preferred.

According to the present invention, the above-mentioned amount of Lewis acid, amount of supported metal catalyst and weight ratio liquid solvent:furfuryl alcohol may be determined at the beginning of step a) and/or may be continuously determined and adjusted during step a).

Determining the amount of Lewis acid, the amount of supported metal catalyst and the weight ratio liquid solvent:furfuryl alcohol at the beginning of step a) is particularly suited to step a) carried out in batch mode. Indeed, in batch mode, the amount of furfuryl alcohol decreases during step a) since furfuryl alcohol is converted during step a) and the amount of MeTHF increases during step a) since it is produced during step a).

Determining and adjusting continuously the amount of Lewis acid, the amount of supported metal catalyst and the weight ratio liquid solvent:furfuryl alcohol during step a) is particularly suited to step a) carried out continuously. The amount of furfuryl alcohol and of MeTHF may be determined and adjusted, respectively, at the inlet and at the outlet of the catalytic reactor carrying out step a) continuously.

According to a very specific embodiment, the metal of the supported metal catalyst may be palladium, the support of the supported metal catalyst may be alumina, the Lewis acid may be lithium tetrafluoroborate and the liquid solvent may be MeTHF.

According to this very specific embodiment, the amount of Lewis acid may be 0.05 mole to 0.065 mole equivalents with respect to furfuryl alcohol, the amount of supported metal catalyst may be 4.5 wt % to 5.5 wt % with respect to furfuryl alcohol and the weight ratio liquid solvent:furfuryl alcohol may be 1:0.3 to 1:2.5, in particular 1:0.5 to 1:1.5.

In this very specific embodiment, the conversion rate of furfuryl alcohol and the selectivity towards MeTHF may be maintained very high when step a) is carried out continuously or repeatedly in batch mode.

According to another very specific embodiment, the metal of the supported metal catalyst may be palladium, the support of the supported metal catalyst may be carbon, the Lewis acid may be iron(II) dodecyl sulfate, iron(III) dodecyl sulfate, Lithium tetrafluoroborate, or mixture thereof and the liquid solvent may be MeTHF.

According to this another very specific embodiment, the amount of Lewis acid may be 0.05 mole to 0.065 mole equivalents with respect to furfuryl alcohol, the amount of supported metal catalyst may be 4.5 wt % to 5.5 wt % with respect to furfuryl alcohol and the weight ratio liquid solvent:furfuryl alcohol may be 1:0.3 to 1:2.5, in particular 1:0.5 to 1:1.5.

The proposed process may further comprise the following steps:
b) separating the catalytic system, in particular the Lewis acid, from the reaction mixture to recover on the one hand the catalytic system, in particular the Lewis acid, and on the other hand a mixture comprising MeTHF, and
c) recycling all or part of the catalytic system, in particular all or part of the Lewis acid, recovered at the end of step b) into step a).

Recycling the catalytic system advantageously improves the industrial viability of the proposed process.

The reaction mixture obtained at the end of step a) comprises MeTHF and the catalytic system. Depending on the conversion rate of furfuryl alcohol and the selectivity towards MeTHF, the reaction mixture may also comprise unreacted furfuryl alcohol and side-products such as 2-methylfuran, tetrahydrofurfuryl alcohol. MeTHF, furfuryl alcohol, the side-products and the Lewis acid are liquid, while the supported metal catalyst is solid. Accordingly, the catalytic system may be separated from the reaction mixture in two times. For example, during step b):
the supported metal catalyst may be first separated from the reaction mixture to recover on the one hand the supported metal catalyst and on the other hand a liquid mixture comprising MeTHF and the Lewis acid, and then
the Lewis acid may be separated from the liquid mixture to recover the Lewis acid on the one hand and the mixture comprising MeTHF on the other hand.

The separation of the supported metal catalyst from the reaction mixture may be carried out by techniques known by the skilled person to separate solid from liquid. Filtration is one of these techniques. For example, filter(s) performing the filtration may be provided at the outlet of the reactor so that the supported metal catalyst may stay in the reactor and the liquid mixture may come out of the reactor to be recovered.

The separation of the Lewis acid from the liquid mixture may be carried out by techniques known by the skilled person to separate liquid from liquid. For example, these techniques are distillation, liquid-liquid extraction, filtration and combinations thereof. The filtration may be membrane filtration.

If necessary MeTHF may be easily separated from unreacted furfuryl alcohol and side-products such as 2-methylfuran, tetrahydrofurfuryl alcohol by techniques known by the skilled person to separate liquid from liquid for instance by distillation. This separation is advantageously facilitated by the fact that MeTHF is the main compound among unreacted furfuryl alcohol and the side-products.

EXAMPLES

General Information

Hydrogenation experiments were performed in either a 15 ml glass micro-reactor (Biotage® Endeavor™ Catalyst Screening System) or a 300 ml stainless steel autoclave (Parr Instruments). Micro-reactor tests were conducted exclusively as batch reactions whereas the autoclave tests were conducted either as a batch process or as a semi-batch process involving slow feeding of one of the raw materials.

Product analysis was performed by gas chromatography (GC) under the following set of conditions: Column type, Zebron ZB-5; Column length, 60 meters; Flame Ionization Detector (FID); Gas Flow Rate, 11 ml/min; Run Time, 20 min; and Temperature Program:
Initial Temperature: 80° C. Maintaining for 2 min
Ramp Rate: 50° C./min
Final Temperature: 280° C. Maintaining for 10 min.

Example 1: Comparative Example

Hydrogenation of Furfuryl Alcohol with Pd/Alumina Catalyst and No Lewis Acid Additive in a Micro-Reactor To a 15 ml glass micro-reactor was added furfuryl alcohol (0.98 g, 10 mmol), 2-methyltetrahydrofuran as liquid solvent (3.0 g), and 5% Pd/alumina catalyst (50 mg). The reactor was sealed and purged 2 times with hydrogen. The reaction mixture was then heated to 60° C., pressurized to 3.5 bar Hydrogen with agitation at 450 rpm. The reaction was allowed to proceed for 3 hours. The reaction was then stopped and allowed to cool to ambient temperature. The mixture was filtered through an Acrodisc (0.7 micron)

syringe filter and analyzed by GC-FID. The conversion and selectivity as inferred by GC analysis are shown in Table 1.

Examples 2 to 15

Hydrogenation of Furfuryl Alcohol with Pd/Alumina Catalyst and a Lewis Acid Additive in a Micro-Reactor To a 15 ml glass micro-reactor was added furfuryl alcohol (0.98 g, 10 mmol), 2-methyltetrahydrofuran as liquid solvent (3.0 g), a Lewis acid (0.55 mmol) and a 5% Pd catalyst (50 mg) from the list shown in Table 1. The reactor was sealed and purged 2 times with hydrogen. The reaction mixture was then heated to 60° C., pressurized to 3.5 bar Hydrogen with agitation at 450 rpm. The reaction was allowed to proceed for 3 hours. The reaction was then stopped and allowed to cool to ambient temperature. The mixture was filtered through an Acrodisc (0.7 micron) syringe filter and analyzed by GC-FID. The conversion and selectivity as inferred by GC analysis are shown in Table 1.

TABLE 1

| Example no. | Supported metal catalyst | Lewis Acid | Conversion (%) | Selectivity, % of converted FA ||||
|---|---|---|---|---|---|---|---|
| | | | | MeF | MeTHF | THFA | Others |
| 1 | 5% Pd/Al$_2$O$_3$ | None | 37.3 | 13.5 | 7.8 | 76.2 | 2.5 |
| 2 | 5% Pd/Al$_2$O$_3$ | FeCl$_3$ | 100 | 14.5 | 76.2 | 1 | 8.2 |
| 3 | | FeCl$_3$•6H$_2$O | 94.4 | 13.3 | 79.5 | 0.8 | 6.4 |
| 4 | | SnCl$_4$•5H$_2$O | 68.2 | 3.9 | 94.8 | 0 | 1.3 |
| 5 | | LiBF$_4$ | 82.7 | 9.8 | 79.5 | 4.2 | 6.5 |
| 6 | | AgOTf | 100 | 1.0 | 83.0 | 8.2 | 7.8 |
| 7 | | Sc(OTf)$_3$ | 92.5 | 2.2 | 86.4 | 1.3 | 10.1 |
| 8 | | Al(OTf)$_3$ | 96.4 | 8.7 | 76.0 | 6.1 | 9.2 |
| 9 | 5% Pd/C | AgOTf | 100 | 6.0 | 72.5 | 10.8 | 10.7 |
| 10 | | LiBF$_4$ | 87.3 | 18.4 | 60.6 | 14.5 | 6.5 |
| 11 | | Fe(II) Dodecyl sulfate | 98.1 | 10.2 | 78.5 | 5.2 | 6.1 |
| 12 | | Fe(III) Dodecyl sulfate | 88.5 | 3.7 | 82.4 | 5.4 | 8.5 |
| 13 | 5% Pd/SiO$_2$ | Zn(OTf)$_2$ | 75.0 | 6.2 | 91.8 | 0.8 | 1.2 |
| 14 | | AgOTf | 100 | 6.8 | 81.8 | 9.4 | 2.0 |
| 15 | 5% Pd/TiO$_2$ | SnCl$_4$ | 68.2 | 3.9 | 94.8 | 0 | 1.3 |

Example 16

Hydrogenation of Furfuryl Alcohol with 5% Pd/Alumina Catalyst and LiBF$_4$ as Lewis Acid in an Autoclave as a Batch Process To a 300 mL stainless steel autoclave was added 5% Pd/alumina as supported metal catalyst (2,5 g, 5 wt % with respect to furfuryl alcohol), lithium tetrafluoroborate as Lewis acid (3.0 g, 32 mmol), furfuryl alcohol (50.0 g, 510 mmol) and 2-methyltetrahydrofuran as liquid solvent (50.0 g). The autoclave was sealed and purged 3 times with hydrogen. The reaction mixture was then heated to 60° C., pressurized to 3.5 bar H$_2$ with agitation at 450 rpm. The reaction was allowed to proceed for 5 hours. The reaction was then stopped and allowed to cool to room temperature. A sample of the mixture was filtered through an Acrodisc (0.7 micron) syringe filter and analyzed by GC-FID. The reaction mixture was filtered through a fritted glass funnel to recover the catalyst.

The conversion and selectivity data from Example 16 are shown in Table 2.

Example 17

Hydrogenation of Furfuryl Alcohol with 5% Pd/Alumina Catalyst and LiBF$_4$ as Lewis Acid in an Autoclave as a Semi-Batch Process To a 300 mL stainless steel autoclave was added 5% Pd/alumina as supported metal catalyst (2,5 g, 5 wt % with respect to furfuryl alcohol), lithium tetrafluoroborate (3.0 g, 32 mmol) and 2-methyltetrahydrofuran (50.0 g). The autoclave was sealed and purged 3 times with hydrogen. The reaction mixture was then heated to 60° C., pressurized to 3.5 bar H$_2$ with agitation at 450 rpm. Furfuryl alcohol (50.0 g, 510 mmol) was pumped into the autoclave using an Eldex metering pump at 0.15 mL/min feed rate. The reaction was allowed to proceed for 6 hours. The reaction was then stopped and allowed to cool to room temperature. A sample of the mixture was filtered through an Acrodisc (0.7 micron) syringe filter and analyzed by GC-FID. The reaction mixture was filtered through a fritted glass funnel to recover the catalyst.

The conversion and selectivity data from Example 17 are shown in Table 2.

TABLE 2

| Example no. | Supported metal catalyst + Lewis acid | Conversion % | Selectivity, % of converted FA ||||
|---|---|---|---|---|---|---|
| | | | MeF | MeTHF | THFA | Others |
| 16 | 5% Pd/Al$_2$O$_3$ + LiBF$_4$ | >99 | 9.4 | 75.6 | 8.2 | 6.8 |
| 17 | 5% Pd/Al$_2$O$_3$ + LiBF$_4$ | >99 | 3.5 | 87.2 | 5.0 | 4.2 |

Example 18

Hydrogenation of Furfuryl Alcohol with 5% Pd/Alumina Catalyst and LiBF$_4$ as Lewis Acid in an Autoclave, Recycling of Pd/Alumina Catalyst in Four Consecutive Semi-Batch Tests so that a Single Charge of Pd/Alumina Catalyst is Used To a 300 mL stainless steel autoclave was added 5% Pd/alumina as supported metal catalyst (2,5 g, 5 wt % with respect to furfuryl alcohol), lithium tetrafluoroborate (1.5 g, 16 mmol) and 2-methyl tetrahydrofuran as liquid solvent (50.0 g). The autoclave was sealed and purged 3 times with hydrogen. The reaction mixture was then heated to 60° C., pressurized to 3.5 bar H$_2$ with agitation at 450 rpm. Furfuryl alcohol (27.0 g, 275 mmol) was pumped into the autoclave using an Eldex metering pump at 0.15 mL/min. The reaction was allowed to proceed for 3 hours. The reaction was then stopped, and the agitation stopped to allow the catalyst to settle. The autoclave was also cooled to room temperature. The reaction mixture was then decanted.

A solution of lithium tetrafluoroborate (1.5 g, 16 mmol) in 2-methyltetrahydrofuran (50.0 g) was added to the autoclave. The autoclave was re-sealed and purged 3 times with hydrogen. The autoclave was then heated to 60° C., pressurized to 3.5 bar H$_2$ with agitation at 450 rpm. Furfuryl alcohol (27.0 g, 275 mmol) was pumped into the autoclave using an Eldex metering pump at 0.15 mL/min. The reaction was allowed to proceed for 3 hours. The reaction was then stopped, and the agitation stopped to allow the catalyst to settle. The autoclave was also cooled to room temperature. The reaction mixture was then decanted.

The conversion and selectivity data from four consecutive semi-batch tests are shown in Table 3.

TABLE 3

| Supported metal catalyst + Lewis acid | Batch n° | Conversion % | Selectivity, % of converted FA | | | |
|---|---|---|---|---|---|---|
| | | | MeF | MeTHF | THFA | Others |
| 5% Pd/Al$_2$O$_3$ + LiBF$_4$ (single charge of Pd/Al$_2$O$_3$ used in 4 consecutive batches) | 1 | 100 | 1.9 | 89.4 | 4.8 | 3.9 |
| | 2 | 100 | 5.1 | 85.1 | 5.7 | 4.1 |
| | 3 | 100 | 2.3 | 86.3 | 6.9 | 4.6 |
| | 4 | 99.2 | 7.0 | 80.1 | 7.4 | 4.8 |

Example 19

Hydrogenation of Furfuryl Alcohol with 5% Pd/Carbon Catalyst and BF3 as Lewis Acid in an Autoclave as a Semi-Batch Process To a 300 mL stainless steel autoclave was added 5% Pd/carbon as supported metal catalyst (2,5 g, 5 wt % with respect to furfuryl alcohol), boron trifluoride monohydrate as Lewis acid (2.8 g, 33 mmol), furfuryl alcohol (50.0 g, 510 mmol) and 2-methyltetrahydrofuran as liquid solvent (50.0 g). The autoclave was sealed and purged 3 times with hydrogen. The reaction mixture was then heated to 55° C., pressurized to 3.5 bar H$_2$ with agitation at 450 rpm. The reaction was allowed to proceed for 9 hours. The reaction was then stopped and allowed to cool to room temperature. A sample of the mixture was filtered through an Acrodisc (0.7 micron) syringe filter and analyzed by GC-FID. The reaction mixture was filtered through a fritted glass funnel to recover the catalyst.

Example 20

Hydrogenation of Furfuryl Alcohol with 5% Pd/Alumina Catalyst and Bis(Oxalato)Boric Acid as Lewis Acid in an Autoclave as a Semi Batch Process To a 300 mL stainless steel autoclave was added 5% Pd/alumina as supported metal catalyst (2,5 g, 5 wt % with respect to furfuryl alcohol), bis(oxalato)boric acid as Lewis acid (6.0 g, 32 mmol), furfuryl alcohol (50.0 g, 510 mmol) and 2-methyltetrahydrofuran as liquid solvent (50.0 g). The autoclave was sealed and purged 3 times with hydrogen. The reaction mixture was then heated to 60° C., pressurized to 3.5 bar H$_2$ with agitation at 450 rpm. The reaction was allowed to proceed for 4 hours. The reaction was then stopped and allowed to cool to room temperature. A sample of the mixture was filtered through an Acrodisc (0.7 micron) syringe filter and analyzed by GC-FID. The reaction mixture was filtered through a fritted glass funnel to recover the catalyst.

The conversion and selectivity data from Examples 17 and 18 are shown in Table 4.

TABLE 4

| Example no. | Supported metal catalyst + Lewis acid | Conversion % | Selectivity, % of converted FA | | | |
|---|---|---|---|---|---|---|
| | | | MeF | MeTHF | THFA | Others |
| 19 | 5% Pd/C + BF$_3$•H$_2$O | >99 | 12.5 | 76 | 6.5 | 5 |
| 20 | 5% Pd/Al$_2$O$_3$ + Bis(oxalato)boric acid | >99 | 26.2 | 62.8 | 3.7 | 7.3 |

The invention claimed is:
1. A process for producing 2-methyltetrahydrofuran from furfuryl alcohol, comprising the following step:
   a) contacting furfuryl alcohol with hydrogen in presence of a catalytic system in a liquid solvent to obtain a reaction mixture comprising 2-methyltetrahydrofuran and the catalytic system,
   wherein the catalytic system comprises a supported metal catalyst and a Lewis acid,
   wherein the Lewis acid is chosen from aluminium triflate, boron trifluoride, bis(oxalato)boric acid, cyanuric chloride, iron trichloride, iron trichloride hexahydrate, iron (II) dodecyl sulfate, iron(III) dodecyl sulfate, lithium tetrafluoroborate, magnesium bromide, magnesium triflate, scandium triflate, silver triflate, tin tetrachloride, tin tetrachloride pentahydrate, zinc tetrafluoroborate, zinc triflate and mixtures thereof.
2. The process according to the claim 1, wherein the amount of Lewis acid is 0.001 mole to 0.20 mole equivalents with respect to furfuryl alcohol.
3. The process according to the claim 1, wherein the supported metal catalyst comprises a metal chosen from chromium, manganese, iron, cobalt, nickel, copper, zinc, molybdenum, ruthenium, rhodium, palladium, tin, platinum and mixtures thereof.

4. The process according to claim 3, wherein the supported metal catalyst comprises a support chosen from alumina ($Al_2O_3$), carbon, hydrotalcite, silica ($SiO_2$), titania ($TiO_2$) and mixtures thereof.

5. The process according to the claim 3, wherein the content of metal in the supported metal catalyst relative to the support is 0.1 wt % to 10 wt %.

6. The process according to the claim 1, wherein the amount of supported metal catalyst is 1 wt % to 25 wt % with respect to furfuryl alcohol.

7. The process according to the claim 1, wherein the liquid solvent is chosen from acetonitrile, dichloroethane, dimethylformamide (DMF), ethanol, ethyl acetate, isopropanol, methanol, methyl tert-butyl ether (MTBE), 2-methyltetrahydrofuran, tetrahydrofuran (THF) and mixtures thereof.

8. The process according to the claim 1, wherein the weight ratio liquid solvent:furfuryl alcohol is 1:10 to 10:1.

9. The process according to the claim 1, wherein, during step a), the pressure is 0.5 bar to 10 bar.

10. The process according to the claim 1, wherein, during step a), the temperature is 0° C. to 100° C.

11. The process according to the claim 1, wherein step a) is carried out in batch mode, in semi-batch mode or continuously.

12. The process according to the claim 1, further comprising the following steps:
  b) separating the catalytic system from the reaction mixture to recover on the one hand the catalytic system and on the other hand a mixture comprising MeTHF, and
  c) recycling all or part of the catalytic system recovered at the end of step b) into step a).

13. The process according to the claim 1, wherein the supported metal catalyst comprises a support chosen from alumina, silica, titania, and mixtures thereof.

14. The process according to the claim 13, wherein the support is alumina.

* * * * *